(12) United States Patent
Morimoto et al.

(10) Patent No.: US 7,956,115 B2
(45) Date of Patent: Jun. 7, 2011

(54) PHENYL ACRYLATE

(75) Inventors: Junji Morimoto, Toyonaka (JP);
Tatsumi Nuno, Toyonaka (JP);
Toyomochi Tamato, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 422 days.

(21) Appl. No.: 12/289,891

(22) Filed: Nov. 6, 2008

(65) Prior Publication Data

US 2009/0118407 A1 May 7, 2009

(30) Foreign Application Priority Data

Nov. 6, 2007 (JP) .................................. 2007-288166

(51) Int. Cl.
*C07C 69/618* (2006.01)
*C08K 5/105* (2006.01)
*F21V 9/00* (2006.01)
(52) U.S. Cl. ..................... 524/287; 560/130; 526/318.1; 252/582
(58) Field of Classification Search .................. 524/287; 560/130; 526/318.1; 252/582
See application file for complete search history.

(56) References Cited

U.S. PATENT DOCUMENTS

2006/0261318 A1* 11/2006 Morimoto et al. ............ 252/582

FOREIGN PATENT DOCUMENTS

JP 2001-228334 8/2001

OTHER PUBLICATIONS

European Search Report dated Apr. 15, 2009 in European Patent Application No. 08 16 8260 corresponding to the present application.

* cited by examiner

*Primary Examiner* — Michael M Bernshteyn
(74) *Attorney, Agent, or Firm* — Wenderoth, Lind & Ponack, L.L.P.

(57) ABSTRACT

The present invention is to provide a light-controlling film giving an excellent haze, and a compound and a composition which enable to produce the film. The invention provides phenyl acrylate represented by the formula (I); a composition comprising the phenyl acrylate and at least two kinds of compounds having a polymerizable carbon-carbon bond in a molecule; and a film obtained by photo-curing the above-mentioned composition.

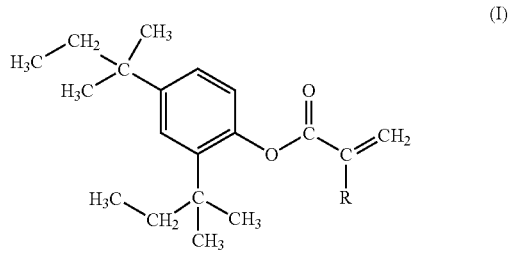

(wherein R represents a methyl group or a hydrogen atom.)

17 Claims, 1 Drawing Sheet

Measurement method of angle dependency of haze

PHENYL ACRYLATE

TECHNICAL FIELD

The present invention relates to phenyl acrylate, a composition comprising phenyl acrylate, and a film obtained by photo-curing the composition.

BACKGROUND ART

A light-controlling film is a film giving a high haze (opacity) by scattering incident light from a specified angle region (opaque angle region), and giving a low haze (transparency) by transmitting incident light from other angle region (transparent angle region). The light-controlling film has been used as a view angle-controlling film by applying the film to a window glass, and a touch panel of a cash dispenser for protecting privacy, and as a view angle-widening film of a flat panel display.

Patent document 1 discloses that, as the light-controlling film, a film obtained by photo-curing a composition comprising 2-hydroxy-3-phenoxypropyl acrylate gives a high haze.

Patent Document 1: JP-A 2001-228334 (Example 1)

DISCLOSURE OF THE INVENTION

An object of the present invention is to provide a compound which enables to produce a light-controlling film giving a further higher haze.

That is, the present invention provides the following [1] to [7].

[1] Phenyl acrylate represented by the formula (I):

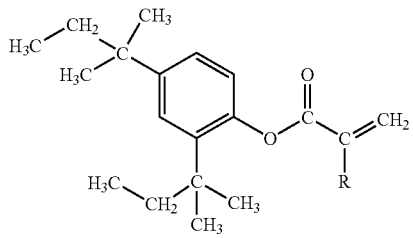

(wherein R represents a methyl group or a hydrogen atom.)

[2] A composition comprising the phenyl acrylate as defined in [1] and at least two kinds of compounds having a polymerizable carbon-carbon bond in a molecule.

[3] The composition according to [2], wherein the at least two kinds of compounds having a polymerizable carbon-carbon bond in a molecule are compounds which, when polymerized into homopolymers, become at least two kinds of homopolymers exhibiting different refractive indices.

[4] The composition according to [2] or [3], wherein the composition further comprises a polymerization initiator.

[5] The composition according to any one of [2] to [4] wherein the at least two kinds of compounds having a polymerizable carbon-carbon bond in a molecule are a compound having a bromine atom and one polymerizable carbon-carbon double bond in a molecule, and urethane (meth)acrylate.

[6] The composition according to any one of [2] to [5], wherein the composition comprises phenyl acrylate as defined in [1] at 0.001 part by weight to 15 parts by weight relative to a total of 100 parts by weight of the phenyl acrylate and at least two kind of compounds having a polymerizable carbon-carbon bond in a molecule.

[7] A film obtained by photo-curing the composition as defined in any one of [2] to [6].

REFERENCE MARKS IN THE DRAWINGS

Figure 1:
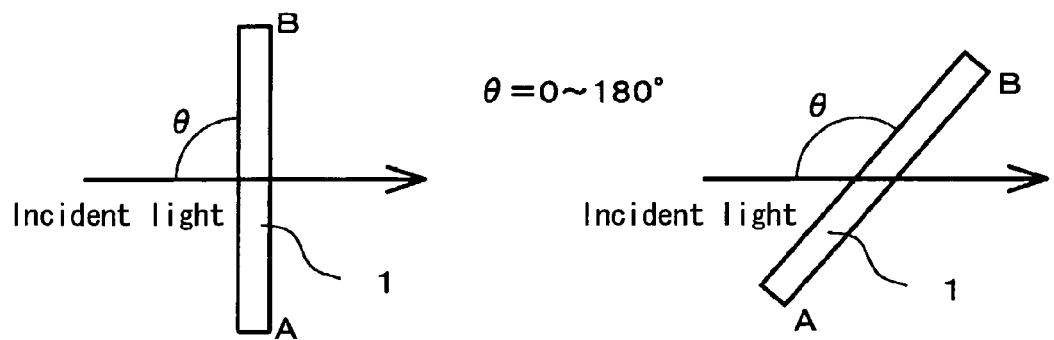
FIG. 1 is a schematic view of a method of measuring angle dependency of a haze.

1 Film on glass plate
2 Light source (rod-like ultraviolet lamp)
3 Light-shielding plate
4 Slit provided in light-shielding plate
5 Conveyer

MODE FOR CARRYING OUT THE INVENTION

The present invention will be described in detail below.

The compound of the present invention is phenyl acrylate represented by the formula (I) (hereinafter, referred to as compound (I) in some cases).

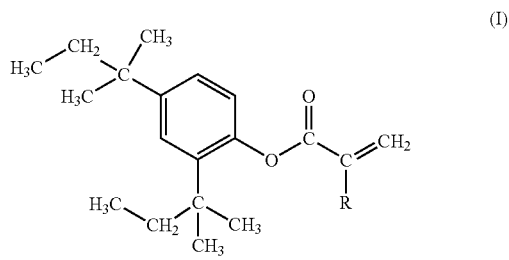

In the formula (I), R represents a methyl group or a hydrogen atom.

The compound (I) is specifically 2,4-di-tert-pentylphenyl acrylate or 2,4-di-tert-pentylphenyl methacrylate, preferably 2,4-di-tert-pentylphenyl acrylate.

A method of producing the compound (I) will be explained using an example of 2,4-di-tert-pentylphenyl acrylate. Examples of the method include a method of esterifying 2,4-di-tert-pentylphenol and acrylic acid by reacting them with phosphorus oxychloride in the presence of an organic base such as triethylamine.

The composition of the present invention is a composition comprising the compound (I) and at least two kinds of compounds having a polymerizable carbon-carbon bond in a molecule, in which the at least two kind compounds having a polymerizable carbon-carbon bond in a molecule contained in the composition are compounds such that homopolymers obtained by homopolymerization of respective compounds have different refractive indices.

The polymerizable carbon-carbon bond herein means an addition-polymerizable carbon-carbon double bond or an addition-polymerizable carbon-carbon triple bond. Specifically, examples thereof include a vinyl group, an allyl group, a styryl group, an acryloyl group, a methacryloyl group, an acrylamide group, a trans-1-oxo-2-butenoxy group, a cinnamoyl group, a butadiene structure, a polymerizable conjugated bond, and a cycloolefin structure such as a cyclopentene ring structure. Among them, the polymerizable carbon-carbon bond is preferably an acryloyl group or a methacryloyl group, particularly preferably an acryloyl group.

Among homopolymers obtained by homopolymerization of each of at least two kinds of compounds having a polymerizable carbon-carbon bond in a molecule, at least two homopolymers have different refractive indices.

As a difference in a refractive index of at least two kinds of homopolymers is larger, a haze of the resulting film becomes higher. The difference in a refractive index is usually 0.01 or larger, preferably 0.02 or larger.

Three or more kinds of compounds having a polymerizable carbon-carbon bond in a molecule may be used in the composition of the present invention and, in such a case, it is enough that refractive indices of at least two kinds of homopolymers among homopolymers of those compounds are different.

A ratio of mixing two kinds of compounds having a polymerizable carbon-carbon bond in a molecule, which give two kinds of homopolymers with different refractive indices, is usually in a range of (1:9) to (9:1) by weight.

Examples of the at least two kinds of compounds having a polymerizable carbon-carbon bond in a molecule include monomers and oligomers.

Examples of the monomers include a compound having one polymerizable carbon-carbon double bond in a molecule, such as tetrahydrofurfuryl acrylate, ethyl carbitol acrylate, dicyclopentenyloxyethyl acrylate, phenyl carbitol acrylate, nonylphenoxyethyl acrylate, 2-hydroxy-3-phenoxypropyl acrylate, ω-hydroxyhexanoyloxyethyl acrylate, acryloyloxyethyl succinate, acryloyloxyethyl phthalate, isobornyl acrylate, 2-ethylhexyl acrylate, lauryl acrylate, 2,2,3,3-tetrafluoropropyl acrylate, N-vinylpyrrolidone, N-acryloylmorpholine, 2-phenylphenyl acrylate, p-cumylphenyl acrylate, diphenylmethyl acrylate, 3-phenoxyphenyl acrylate, and methacrylate monomers corresponding to these acrylates, and compounds having are polymerizable carbon-carbon double bond in a molecule such as styrene, and ethylene.

Different examples of the monomers include compounds having a bromine atom and one polymerizable carbon-carbon double bond in a molecule, such as 2,4,6-tribromophenoxyethyl acrylate and 2,4,6-tribromophenyl acrylate (hereinafter, referred to as bromo-type (meth)acrylate in some cases).

Further examples thereof include compounds having a plurality of polymerizable carbon-carbon double bonds in a molecule, such as bisphenol A diacrylate, triethylene glycol diacrylate, polyethylene glycol diacrylate, neopentyl glycol diacrylate, 1,6-hexanediol diacrylate, hydrogenated dicyclopentadienyl diacrylate, trimethylolpropane triacrylate, pentaerythritol hexacrylate, ethylene oxide-modified bisphenol A diacrylate, trisacryloxy isocyanurate, polyfunctional epoxy acrylate and polyfunctional urethane acrylate, methacrylates corresponding to these acrylates, diethylene glycol bisallyl carbonate, divinylbenzene, butadiene, and triallyl isocyanurate.

Examples of the oligomers include polyfunctional acrylates such as polyester acrylates, polyol polyacrylates, modified polyol polyacrylates, polyacrylates having isocyanuric acid skeletons, melamine acrylates, polyacrylates having hydantoin skeletons, polybutadiene acrylates, epoxy acrylates, and urethane acrylates; and methacrylates corresponding to these acrylates. Examples of the urethane acrylate oligomers include those produced by an addition reaction of polyisocyanates, polyols, and 2-hydroxyalkyl(meth)acrylates. Examples of the polyisocyanates are toluene diisocyanate, isophorone diisocyanate, trimethylhexamethylene diisocyanate, and hexamethylene diisocyanate. Examples of the polyols include polyether polyols such as polyethylene glycol, polypropylene glycol, and polytetramethylene glycol.

The at least two kinds of compounds having a polymerizable carbon-carbon bond in a molecule may be polymerized in advance and used as an oligomer or a polymer.

The at least two kinds of compounds having a polymerizable carbon-carbon bond in a molecule in the composition of the present invention are preferably bromo-type (meth)acrylate and urethane acrylate oligomers.

The content of the compound (I) in the composition of the present invention is 0.001 part by weight or more and 15 parts by weight or less, preferably 0.01 part by weight or more and 12 parts by weight or less relative to a total of 100 parts by weight of the composition. The content is particularly preferably 0.1 part by weight or more and 8 parts by weight or less since a minimum value of a haze curve in an opaque angle region of the resulting film is large, and an opaque angle region is widened. When the compound (I) is contained at an amount of 0.01 part by weight or more, the resulting film tends to give a further higher haze in an opaque angle region, being preferable. And, when the amount is 15 parts by weight or less, the resulting film tends to give a sufficiently low haze in a transparent angle region, being preferable.

The composition of the present invention may further contain polymers such as polypropylene, polyethylene, polystyrene, polymethyl methacrylate, polyethylene oxide, polyvinylpyrrolidone, polyvinyl alcohol and nylon, organic chemicals such as toluene, n-hexane, cyclohexane, methyl alcohol, ethyl alcohol, acetone, methyl ethyl ketone, tetrahydrofuran, ethyl acetate, dimethylformamide, dimethylacetamide and acetonitrile, organic halide compounds, organic silicon compounds, and plastic additives such as plasticizers and stabilizers in addition to the compound (I) and at least two kinds of compounds having a polymerizable carbon-carbon bond in a molecule, as far as light controllability is not inhibited.

The film of the present invention is obtained by photocuring the composition of the present invention. Examples of a production method thereof include a method of coating the composition of the present invention on a substrate such as a glass plate and a polyethylene terephthalate plate to obtain a film-like composition (uncured state) and, thereafter, photocuring the resulting composition; and a method of enclosing the composition of the present invention in a cell to obtain a film-like composition (uncured state) and, thereafter, photocuring the resulting composition.

The film-like composition in the uncured state is usually adjusted to have a thickness of about 25 μm to 1000 μm, a width of 5 cm to 300 cm, and a length of 5 cm to several hundred meters.

The composition from which oxygen is insulated just like the composition obtained by enclosing in a cell does not necessarily require a photopolymerization initiator, however, a photopolymerization initiator is mixed in advance in order to improve the curability in the case of a method of coating on a substrate.

Examples of the photopolymerization initiator include benzophenone, benzil, Michler's ketone, 2-chlorothioxanthone, 2,4-diethylthioxanthone, benzoin methyl ether, benzoin ethyl ether, diethoxy acetophenone, benzyl dimethyl ketal, 2-hydroxy-2-methylpropiophenone, and 1-hydroxycyclohexyl phenyl ketone.

When the photopolymerization initiator is added to the composition, the mixing amount is usually about 0.01 to 5 parts by weight, and preferably about 0.1 to 3 parts by weight relative to 100 parts by weight of the film-like composition.

Figure 2:
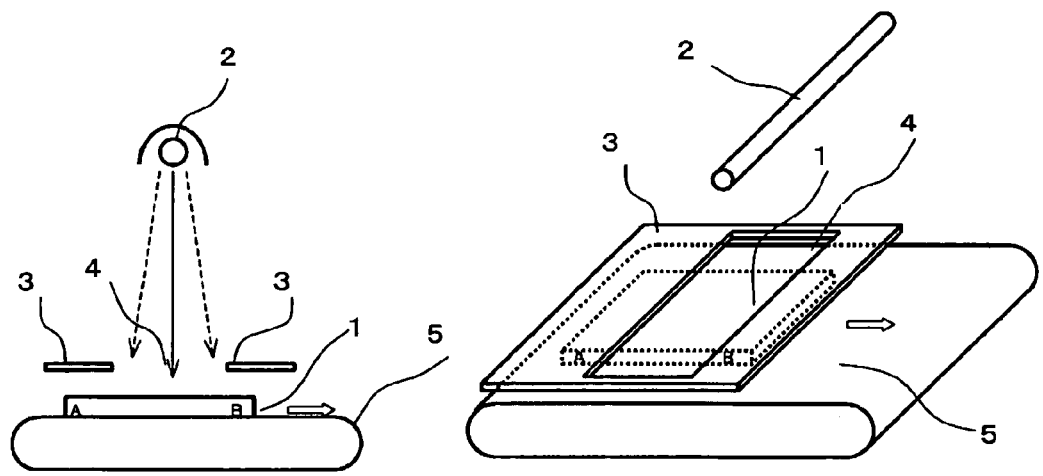
FIG. 2 is a side view of an ultraviolet-curing apparatus (left), and a perspective of the ultraviolet-curing apparatus (right).

Examples of a method of photopolymerization include a method of irradiating light in the perpendicular direction through a slit 4 of a light shielding plate 3 from a rod-like light source 2 as shown in an ultraviolet ray curing apparatus of FIG. 2, mounting the film-like composition 1, coated on a glass plate, on a conveyer 5, and gradually curing this while moving the plate at about 0.01 to 10 m/min, preferably about 0.1 to 5 m/min.

Examples of the ultraviolet light source include a high pressure mercury lamp and a metal halide lamp, and examples of the form of the light source include linear light sources such as a simple rod-like light source, a large number of point light sources arranged continuously in the linear state, and a light source such that the composition is scanned (irradiation of light to one point at a position to be irradiated from a large number of different angles while moving light linearly) with light such as laser beam by using a rotary mirror or a concave mirror. Among them, the rod-like light source is preferable because it is handy.

The film of the present invention can be used as a laminate by covering on or a applying to a transparent substrate such as a glass plate and other plastic sheets. The resultant laminate can be used, for example, as an optical film of windows of construction materials, vehicular windows, mirrors, outer walls for greenhouses, flat panel displays, and rear projection displays.

According to the present invention, a compound which enables to produce a light-controlling film giving a further higher haze can be provided.

EXAMPLES

The present invention will be described in more detail with reference to Examples.

A haze is a value obtained by measuring the total light transmittance and diffusion light transmittance of a film at a distance of 4 cm from the center of the film to an integrating sphere by using an integrating-sphere type light transmittance measuring apparatus (Haze-gard plus 4725, manufactured by Gardner) and calculating according to the following equation.

$$\text{Haze (\%)} = \frac{\text{Diffusion light transmittance (\%)}}{\text{Total light transmittance (\%)}} \times 100$$

Diffuse transmittance =

Total light transmittance − parallel light transmittance

The angle dependency of a haze in the film was measured as follows. That is, the above-mentioned haze is measured at every angle while the angle θ of incident light to a test piece 1 of a film is changed in a range of 0 to 180° as shown in FIG. 1. The angle θ is set to be 0° in the direction parallel to the plane of the test piece 1 and 90° in the direction of the normal line of the test piece 1, and rotation of the test piece 1 is carried out in such the direction that the angle dependency of a haze becomes a maximum. A and B in FIG. 1 are symbols to make the corresponding portions of the test piece 1 understood for the left drawing of FIG. 1 (the case of incident light from the perpendicular direction to the test piece 1:θ=90°) and the right drawing of FIG. 1 (the case of incident light from an oblique direction).

Example 1

A photo-curable composition containing 40 parts by weight of a urethane acrylate oligomer obtained by a reaction of polypropylene glycol with an average molecular weight of about 3,000 with toluene diisocyanate hexamethylene diisocyanate and 2-hydroxyethyl acrylate (compound (2), the refractive index of the homopolymer of the compound (2) was 1.460), 55 parts by weight of 2,4,6-tribromophenyl acrylate (compound (1), the refractive index of the homopolymer of the compound (1) was 1.58), 5 parts by weight of 2,4-di-tert-pentylphenyl acrylate (compound (I-1)), and 1.5 parts by weight of 2-hydroxy-2-methylpropiophenone (photopolymerization initiator) was coated in a thickness of 240 μm to on a PET film of a thickness of 188 μm which had been applied to a glass plate. A rod-like high pressure mercury lamp of 80 W/cm was set at a portion 50 cm above the resulting film-like composition (uncured state), light was irradiated through a light shielding plate having a slit to the entire surface of the coated film (see FIG. 2) while moving the coated film-bearing polyethylene terephthalate/glass plate transversely at a speed of 1.0 m/min to obtain a film. The incident light angle dependency of a haze was measured as shown in FIG. 1. The maximum haze (%) calculated from the obtained angle dependent haze curve is shown in Table 1.

Example 2

A film was obtained according to the same manner as that of Example 1, except that 50 parts by weight of 2,4,6-tribromophenyl acrylate (compound (1)) and 10 parts by weight of 2,4-di-tert-pentylphenyl acrylate (compound (I-1)) were mixed in place of 55 parts by weight of 2,4,6-tribromophenyl acrylate (compound (1)) and 5 parts by weight of 2,4-di-tert-pentylphenyl acrylate (compound (I-1)). The results are shown in Table 1.

Comparative Example 1

A film was obtained according to the same manner as that of Example 2, except that 10 parts by weight of 2-hydroxy-3-phenoxypropyl acrylate (compound (I')) was mixed in place of 10 parts by weight of 2,4-di-tert-pentylphenyl acrylate (compound (I)). The results are shown in Table 1.

TABLE 1

| | Compound (1) | Compound (2) | Compound (I-1) | Compound (I') | Maximum haze(%) |
|---|---|---|---|---|---|
| Example 1 | 55 Parts by weight | 40 Parts by weight | 5 Parts by weight | 0 Parts by weight | 86.4 |
| Example 2 | 50 Parts by weight | 40 Parts by weight | 10 Parts by weight | 0 Parts by weight | 78.7 |
| Comparative Example 1 | 50 Parts by weight | 40 Parts by weight | 0 Parts by weight | 10 Parts by weight | 75.8 |

Compound (1): 2,4,6-Tribromophenyl acrylate
Compound (2): Urethane acrylate oligomer
Compound (I-1): 2,4-di-tert-Pentylphenyl acrylate
Compound (I'): 2-Hydroxy-3-phenoxypropyl acrylate Industrial Applicability According to the present invention, a compound which enables to produce a light-controlling film giving a further lighter haze can be provided.

The invention claimed is:
1. Phenyl acrylate represented by the formula (I):

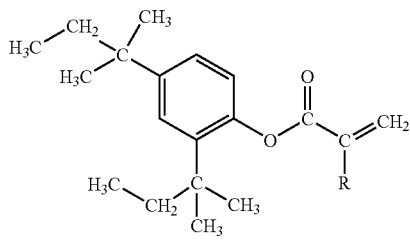

(wherein R is a methyl group or a hydrogen atom.)

2. A composition comprising the phenyl acrylate as defined in claim 1 and at least two kinds of compounds having a polymerizable carbon-carbon bond in a molecule.

3. The composition according to claim 2, wherein the at least two kinds of compounds having a polymerizable carbon-carbon bond in a molecule are compounds which, when polymerized into homopolymers, become homopolymers exhibiting different refractive indices.

4. The composition according to claim 2, wherein the composition further comprises a polymerization initiator.

5. The composition according to claim 2, wherein the at least two kinds of compounds having a polymerizable carbon-carbon bond in a molecule are a compound having a bromine atom and one polymerizable carbon-carbon double bond in a molecule, and urethane (meth)acrylate.

6. The composition according to claim 2, wherein the composition comprises phenyl acrylate as defined in claim 1 at 0.001 part by weight to 15 parts by weight relative to a total of 100 parts by weight of the phenyl acrylate and the at least two kinds of compounds having a carbon-carbon bond in a molecule.

7. A film obtained by photo-curing the composition as defined in claim 2.

8. The composition according to claim 3, wherein the composition further comprises a polymerization initiator.

9. The composition according to claim 3, wherein the at least two kinds of compounds having a polymerizable carbon-carbon bond in a molecule are a compound having a bromine atom and one polymerizable carbon-carbon double bond in a molecule, and urethane (meth)acrylate.

10. The composition according to claim 4, wherein the at least two kinds of compounds having a polymerizable carbon-carbon bond in a molecule are a compound having a bromine atom and one polymerizable carbon-carbon double bond in a molecule, and urethane (meth)acrylate.

11. The composition according to claim 3, wherein the composition comprises phenyl acrylate as defined in claim 1 at 0.001 part by weight to 15 parts by weight relative to a total of 100 parts by weight of the phenyl acrylate and the at least two kinds of compounds having a carbon-carbon bond in a molecule.

12. The composition according to claim 4, wherein the composition comprises phenyl acrylate as defined in claim 1 at 0.001 part by weight to 15 parts by weight relative to a total of 100 parts by weight of the phenyl acrylate and the at least two kinds of compounds having a carbon-carbon bond in a molecule.

13. The composition according to claim 5, wherein the composition comprises phenyl acrylate as defined in claim 1 at 0.001 part by weight to 15 parts by weight relative to a total of 100 parts by weight of the phenyl acrylate and the at least two kinds of compounds having a carbon-carbon bond in a molecule.

14. A film obtained by photo-curing the composition as defined in claim 3.

15. A film obtained by photo-curing the composition as defined in claim 4.

16. A film obtained by photo-curing the composition as defined in claim 5.

17. A film obtained by photo-curing the composition as defined in claim 6.

* * * * *